United States Patent
Saur et al.

(10) Patent No.: US 12,102,386 B2
(45) Date of Patent: Oct. 1, 2024

(54) METHOD FOR ACQUIRING DATA WITH THE AID OF SURGICAL MICROSCOPY SYSTEMS

(71) Applicant: Carl Zeiss Meditec AG, Jena (DE)

(72) Inventors: Stefan Saur, Aalen (DE); Alexander Urich, Munich (DE)

(73) Assignee: Carl Zeiss Meditec AG, Jena (DE)

( * ) Notice: Subject to any disclaimer, the term of this patent is extended or adjusted under 35 U.S.C. 154(b) by 760 days.

(21) Appl. No.: 17/241,844

(22) Filed: Apr. 27, 2021

(65) Prior Publication Data
US 2021/0330183 A1    Oct. 28, 2021

(30) Foreign Application Priority Data
Apr. 28, 2020   (DE) .......................... 102020111584.9

(51) Int. Cl.
*A61B 3/10*   (2006.01)
*A61B 3/13*   (2006.01)
(Continued)

(52) U.S. Cl.
CPC ............... *A61B 3/102* (2013.01); *A61B 3/13* (2013.01); *G02B 21/0012* (2013.01); *G06N 20/00* (2019.01)

(58) Field of Classification Search
CPC .......... A61B 3/102; A61B 3/13; A61B 19/00; A61B 19/50; A61B 19/56; G02B 21/0012;
(Continued)

(56) References Cited

U.S. PATENT DOCUMENTS

2011/0267340 A1* 11/2011 Kraus ................ A61B 3/102
                                                             345/419
2017/0103512 A1   4/2017 Mailhe et al.
(Continued)

FOREIGN PATENT DOCUMENTS

CN    108042090 A    5/2018
DE    102019113493 A1    11/2019
(Continued)

OTHER PUBLICATIONS

Examiner provided machine translation of CN 108042090 (Year: 2018).*
(Continued)

*Primary Examiner* — Tuyen Tra
*Assistant Examiner* — Rahman Abdur
(74) *Attorney, Agent, or Firm* — Honigman LLP; Brett A. Krueger

(57) ABSTRACT

A method for acquiring data with the aid of a surgical microscopy system comprises recording a data set having a multiplicity of images and deciding whether or not the new data set ought to be stored in a data memory of a database. The decision is taken by an existing classifier. A new classifier is determined on the basis of training data which comprise the data sets stored in the data memory of the database and/or comprise data obtained from the data sets stored in the data memory of the database. The new classifier is then used instead of the existing classifier when deciding whether a subsequently recorded new data set ought to be stored.

18 Claims, 2 Drawing Sheets

(51) Int. Cl.
*G02B 21/00* (2006.01)
*G06N 20/00* (2019.01)

(58) Field of Classification Search
CPC .. G02B 21/0056; G02B 21/365; G06N 20/00;
G06N 3/02; G06N 5/01; G16H 50/20;
G16H 30/20; G16H 30/40
USPC ........................................................ 351/205
See application file for complete search history.

(56) References Cited

U.S. PATENT DOCUMENTS

| | | |
|---|---|---|
| 2018/0144466 A1 | 5/2018 | Hsieh et al. |
| 2019/0350564 A1 | 11/2019 | Gajdos et al. |
| 2020/0019823 A1 | 1/2020 | Wang |
| 2020/0051239 A1 | 2/2020 | Braun et al. |
| 2020/0129263 A1 | 4/2020 | Izadyyazdanabadi et al. |

FOREIGN PATENT DOCUMENTS

| | | |
|---|---|---|
| DE | 102018128806 A1 | 1/2020 |
| WO | 2018152248 A1 | 8/2018 |

OTHER PUBLICATIONS

German Office Action, with translation thereof, for corresponding DE application No. 10 2020 111 584.9 dated Jan. 27, 2021, 18 pages.

\* cited by examiner

METHOD FOR ACQUIRING DATA WITH THE AID OF SURGICAL MICROSCOPY SYSTEMS

CROSS-REFERENCE TO RELATED APPLICATIONS

This application claims priority of German Patent Application No. 10 2020 111 584.9 filed on Apr. 28, 2020, the contents of which are incorporated herein.

TECHNICAL FIELD

The present disclosure relates to methods for acquiring in particular annotated data with the aid of surgical microscopy systems.

BACKGROUND

The present application is related to the further patent application filed on the same date in the name of the present applicant, which is entitled "Method for acquiring annotated data with the aid of surgical microscopy systems" and is incorporated by reference in its entirety in the present application.

In the field of medicine, it is necessary to take a variety of decisions based on the analysis of data. By way of example, said decisions may comprise diagnoses regarding the presence or absence of a state on the basis of chemical or physical analyses, for example, decisions about treatments to be carried out or use of aids on the basis of diagnoses and other information. Machine learning techniques are increasingly being used to support such decisions. Machine learning techniques comprise the use of instruments such as of a classifier, for example, which, on the basis of features that have been input, can effect an assignment of the features that have been input to classes of a feature space. Such classifiers are trained using realistic data, and so the quality of the classifications effected by the classifier improves as the amount of realistic data available and the quality of the realistic data available increase. Accordingly, it is desirable to obtain data for training machine learning instruments in large amounts and with good quality.

However, obtaining large amounts of high-quality data is not easy, since the existing processes in the medical field are primarily designed for optimum treatment of patients and reduction of costs. Acquiring data that form the basis for developing machine learning instruments can be effected in parallel with the progression of the existing medical processes only with additional outlay and can even disturb these processes. Acquiring data suitable for training machine learning instruments thus intrinsically proves to be a technical problem.

Accordingly, it is an object of the present disclosure to propose a method for acquiring data in the medical field which are suitable for training a machine learning instrument, such as a classifier, for instance.

The disclosure therefore proposes a method for acquiring annotated data with the aid of surgical microscopy systems. Large numbers of surgical microscopy systems are installed in hospitals and doctors' practices and are used for treating patients. In this case, the surgical microscopy systems in the course of their use on patients can continuously record images of the regions of the patients in need of treatment. Furthermore, sequences of images recorded by the surgical microscopy systems also document measures actually performed on the treated patient. The images recorded by a surgical microscopy system are thus data having a high relevance to training a machine learning instrument.

It is thus conceivable to record all data that arise during the operation of the surgical microscopy system, to store them in a database and subsequently to use them as data with which machine learning instruments are trained. However, it has been found that this possibility is subject to some technical limitations. In this regard, an enormous amount of data is generated by a surgical microscope. The data are for example videos consisting of a plurality of frames having a very high resolution. The data can furthermore be for example volume images having a multiplicity of slice images, which in turn have a high resolution. Furthermore, the data can represent for example a multiplicity of OCT scans, which in turn have a high resolution. If the data acquired by many surgical microscopy systems are intended to be stored in a database in order to train machine learning instruments on the basis of the data stored in the database, then these data have to be transmitted from the individual surgical microscopy systems to a data memory of the database that by its nature is arranged spatially remotely from many of the surgical microscopy systems. Given the present-day customary bandwidth of Internet connections for uploading data, it is difficult to transfer all of the data that arise during the operation of the surgical microscopy system to a central database. Even with an increasing bandwidth of the data connections in the future, this problem will probably persist since the amount of data generated by a surgical microscopy system during operation will also increase.

Furthermore, a surgical microscopy system is used for different purposes and different types of medical interventions that are carried out with different frequencies. With regard to training machine learning instruments, the data concerning medical interventions that are carried out frequently are just as valuable as data concerning medical interventions that are carried out more rarely. However, it is possible that data which contain to a dominant extent similar contents with respect to medical interventions that are carried out frequently are less suitable for training machine learning instruments than data which contain contents with respect to medical interventions that are carried out frequently and contents with respect to medical interventions that are carried out more rarely in a balanced ratio.

In accordance with exemplary embodiments, therefore, not all of the data acquired by means of the surgical microscopy system are stored in a data memory of a database that is arranged remotely from the surgical microscope, but rather only those data which are expected to be able, with respect to the totality of the data stored in the data memory, to make a significant contribution with regard to the training of machine learning instruments with these data.

In accordance with exemplary embodiments, the method for acquiring data with the aid of a surgical microscopy system comprises recording a new data set comprising a multiplicity of images by means of the surgical microscopy system. Said new data set is analysed, and a decision is taken to the effect of whether or not the new data set ought to be stored in the data memory of the database. For this analysis and for taking the decision, an existing classifier can be used, which takes the decision on the basis of the new data set.

By way of example, the analysis of the new data set includes whether the data set comprises an image content of interest. In this regard, by means of automated image analysis, for example, it is possible to identify whether tissue that is intended to be subjected to an operation is contained in an image of the data set, or whether the image satisfies predetermined image quality criteria (for example brightness, contrast). The automated assessment of the new data set that is necessary for this purpose can be carried out (as a partial process) by the existing classifier.

On the basis of the analysis of the new data set, that is to say on the basis of a result of the analysis, the existing classifier decides whether the data set is suitable for being able to make a significant contribution with regard to the training of machine learning instruments. If the new data set documents for example an operation which is carried out rarely or which is still taken into account to a small extent in a training data set for training machine learning instruments, the classifier can decide that the new data set can make a significant contribution with regard to the training of machine learning instruments; accordingly, the classifier decides that the new data set ought to be stored in the data memory of the database. However, if the new data set documents for example an operation which is carried out often or which is already taken into account to a sufficient extent in a training data set for training machine learning instruments, the classifier can decide that the new data set cannot make a significant contribution with regard to the training of machine learning instruments. Accordingly, the classifier decides that the new data set ought not to be stored in the data memory of the database.

In accordance with exemplary embodiments, the classifier can furthermore take the decision on the basis of further information obtained for example from a user who inputs this information into the surgical microscopy system via a user interface.

The classifier can furthermore take the decision on the basis of further information that has already been stored in the surgical microscopy system, for example, or said information may have been stored in an information management system of a hospital in which the surgical microscopy system is situated and/or of a company that manufactured the surgical microscopy system. Such an information management system can be a central database with localized data memories which is arranged at the institution that operates the information management system, such as a hospital or manufacturer, for instance. However, such an information management system can also be a distributed database system which stores associated data at different locations, wherein specific data can be stored only to a lesser extent at specific locations in order to comply with possible data protection rules.

Such further information can denote for example a type of a medical intervention, an age, a sex and/or a state of health of a patient on whom the medical intervention is performed, a quality of tissue imaged in the images, a characteristic of the user, such as the latter's professional experience, for instance, a location at which the surgical microscopy system is situated and/or a characteristic of the use history of the surgical microscopy system, such as, for example, the information that a relevant surgical microscopy system is principally used for fluorescence examinations.

In accordance with exemplary embodiments, on the basis of the decision of the classifier, the at least one new data set is stored in the data memory of the database if it was decided that the at least one data set ought to be stored, and the at least one new data set is not stored in the data memory if it was decided that the at least one data set ought not to be stored.

In accordance with exemplary embodiments, the storage in the data memory of the database is effected by the at least one new data set being transferred from the surgical microscopy system to the database via a communication network (remote data transfer) and the database storing the data set that has been transferred via the communication network in the data memory of the database. For this purpose, the surgical microscopy system comprises a transmitter configured to transmit data (for example the new data set) via the communication network. Furthermore, for this purpose, the database (or a system that provides the database) comprises a receiver configured to receive data transmitted via the communication network.

The communication network can be for example a local communication network (for example "local area network" (LAN)), a global communication network (for example "wide area network" (WAN)) or the like or a combination thereof. By way of example, the communication network is at least partly provided by the Internet.

In accordance with exemplary embodiments, the method comprises determining a new classifier on the basis of training data which comprise the data sets stored in the data memory of the database and/or comprise data obtained from the data sets stored in the data memory of the database, and using the new classifier instead of the existing classifier when deciding whether or not a subsequently recorded new data set ought to be stored in the data memory.

Determining the new classifier can be effected for example at regular time intervals or whenever a predetermined number of new data sets have been stored in the data memory of the database.

By virtue of the new classifier being used when deciding whether or not the subsequently recorded new data set ought to be stored in the data memory, this decision also becomes dependent on the data sets that have already been stored in the data memory. It is thus possible to dispense with the storage of a new data set which is similar to already stored data sets and, in comparison therewith, would supply only little additional information. This new data set that is not stored will not load the network connections having limited transfer capacity. Furthermore, in the case of the data sets stored in the data memory, it is thereby possible to maintain a balanced ratio of data sets concerning frequently recurring medical interventions and data sets concerning interventions that are carried out more rarely.

By virtue of the use of the new classifier when deciding whether or not a new data set ought to be stored, the decisions regarding the storage of the new data sets also become dependent on the already stored data sets since the new classifier is determined on the basis of the already stored data sets. This is achieved, however, without the stored data sets having to be accessed in the decision process necessary for this purpose, which would be very complex on account of the large data volume of the data sets. However, it is possible for the analyses of the data sets which are necessary for determining the classifier directly or for generating training data for determining the classifier to be carried out at the location of the data memory of the data sets, such that a complex remote transfer of the data sets is not necessary for these purposes. It is then merely necessary to transfer the newly determined classifier to the location of the surgical microscopy system. This can be done for example by numerical parameters that represent the new classifier being transferred to the surgical microscopy system. If the classifier which analyses the new data set and takes the decision about storing and not storing the new data set is a classifier which uses a neural network of a given topology, said parameters can be for example weights of said neural network.

In accordance with exemplary embodiments, an annotation is assigned to each of the data sets stored in the data memory. The annotations assigned to the stored data sets can be obtained in various ways. By way of example, the annotations can be ascertained on the basis of an analysis of the data sets automatically with the aid of a machine learning instrument created beforehand, such as a classifier, for example. Furthermore, the annotations can also be obtained by human experts who consider the data sets, that is to say the images contained in the data sets, and take account of various further items of information, such as annotations already present with respect to the data sets, for instance, which were assigned for example to new data sets prior to transfer into the data memory.

In accordance with exemplary embodiments herein, the new classifier is also determined on the basis of the annotations assigned to the stored data sets by virtue of the training data comprising the annotations, for example.

In accordance with exemplary embodiments, a significance is assigned to each of the data sets stored in the data memory.

In accordance with exemplary embodiments herein, the new classifier is also determined on the basis of the significances assigned to the stored data sets by virtue of the training data comprising the significances, for example.

As a result, it is possible, when deciding whether or not a new data set ought to be stored, to give preference to those data sets which have the higher expectable information content with regard to the training of the machine learning instrument. By way of example, data sets concerning medical interventions that are carried out more frequently are then stored comparatively more rarely than data sets concerning medical interventions that are carried out less frequently.

In accordance with exemplary embodiments, assigning annotations and/or significances to the data sets stored in the data memory is repeated after a plurality of new data sets have been stored in the data memory. This creates a system which adapts to the practical use of the surgical microscopy systems and discriminates against data sets which give reason to expect no or only little additional information content with regard to storage in the data memory, while data sets which give reason to expect a high information content or are distinguished by a combination of assigned annotations which are not assigned to a data set or only assigned to a few data sets stored in the data memory are preferred with regard to storage.

In accordance with exemplary embodiments, the new classifier is determined with the aim that when significances are once again assigned to the data sets, the significance newly assigned to a respective data set is lower than the significance previously assigned to this data set.

In accordance with exemplary embodiments, a machine learning instrument is trained on the basis of the data stored in the database. The machine learning instrument can be a classifier, for example, the algorithm of which comprises for example a neural network and a decision tree or the like. By way of example, a clinical hypothesis can be validated by means of the machine learning instrument. Furthermore, the trained machine learning instrument can also be the classifier used to take the decision as to whether or not a new data set ought to be stored in the data memory.

BRIEF DESCRIPTION OF DRAWINGS

Embodiments of the disclosure are explained in greater detail below with reference to figures, in which.

DETAILED DESCRIPTION

Figure 1:
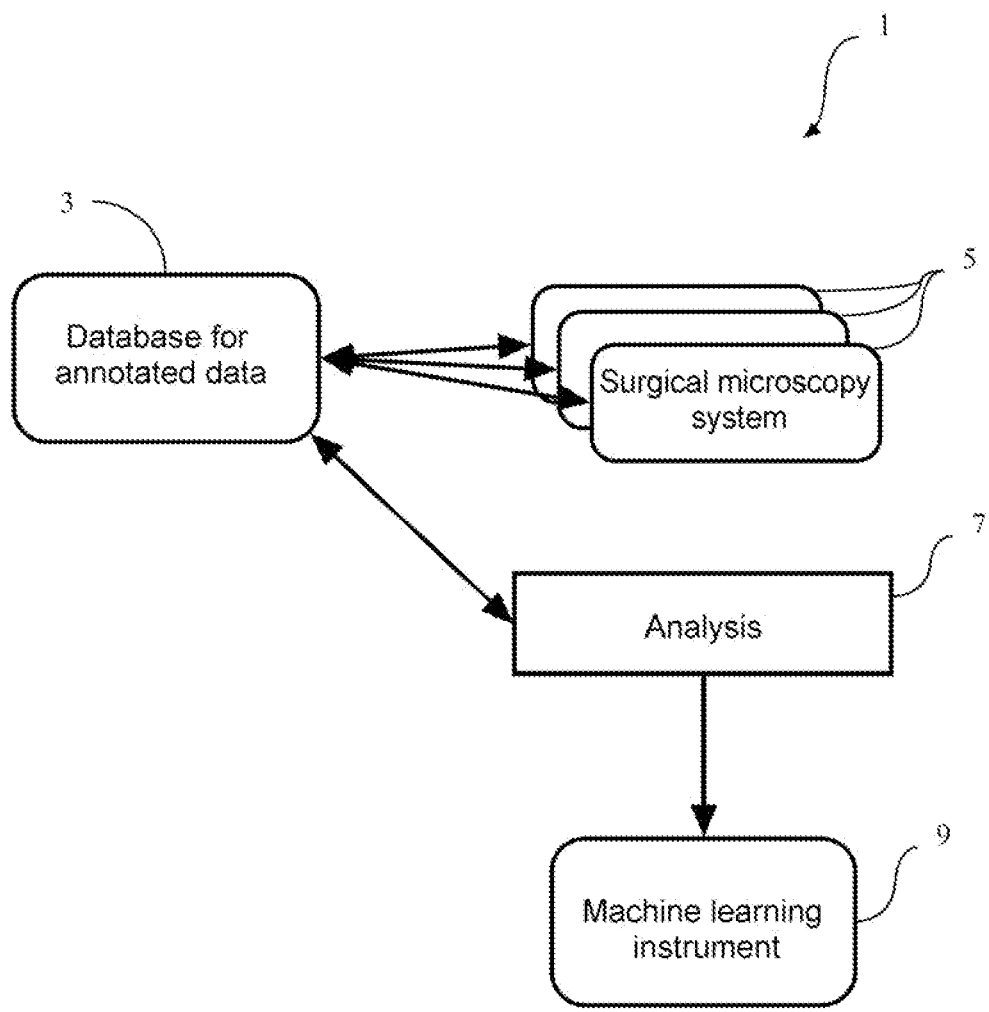
FIG. 1 shows a diagram for elucidating a method for acquiring annotated data in accordance with one embodiment, and a system 1 for carrying out the method.

FIG. 1 is a diagram for elucidating a method for acquiring data for machine learning with the aid of surgical microscopy systems. A system 1 for acquiring data for machine learning comprises a database 3 for annotated data and a plurality of surgical microscopy systems 5, which record data sets that can be stored in the database 3. The data stored in the database 3 are analysed in an analysis module 7 in order to generate a machine learning instrument on the basis of the analysis, said instrument being a classifier 9 in the example shown in FIG. 1. The analysis of the data for generating the machine learning instrument can also comprise processes which can be referred to as "training" of the machine learning instrument, such as the classifier 9, for example.

The surgical microscopy systems 5 typically comprise a surgical microscope with the microscopy optics and with sensors, such as cameras or OCT scanners, for instance, a stand for mounting the surgical microscope and a control system for controlling the surgical microscope and for providing functionalities. The control system can provide user interfaces, databases and remote data connections, inter alia. Not all of the components of the surgical microscopy system 5 have to be arranged together with the surgical microscope thereof in a room, for example.

The data sets generated by the surgical microscopy systems 5 typically comprise a multiplicity of images. The data sets can thus be, for example, videos having a plurality of frames, volume images having a plurality of slice images, and sets of OCT scans.

Figure 2:
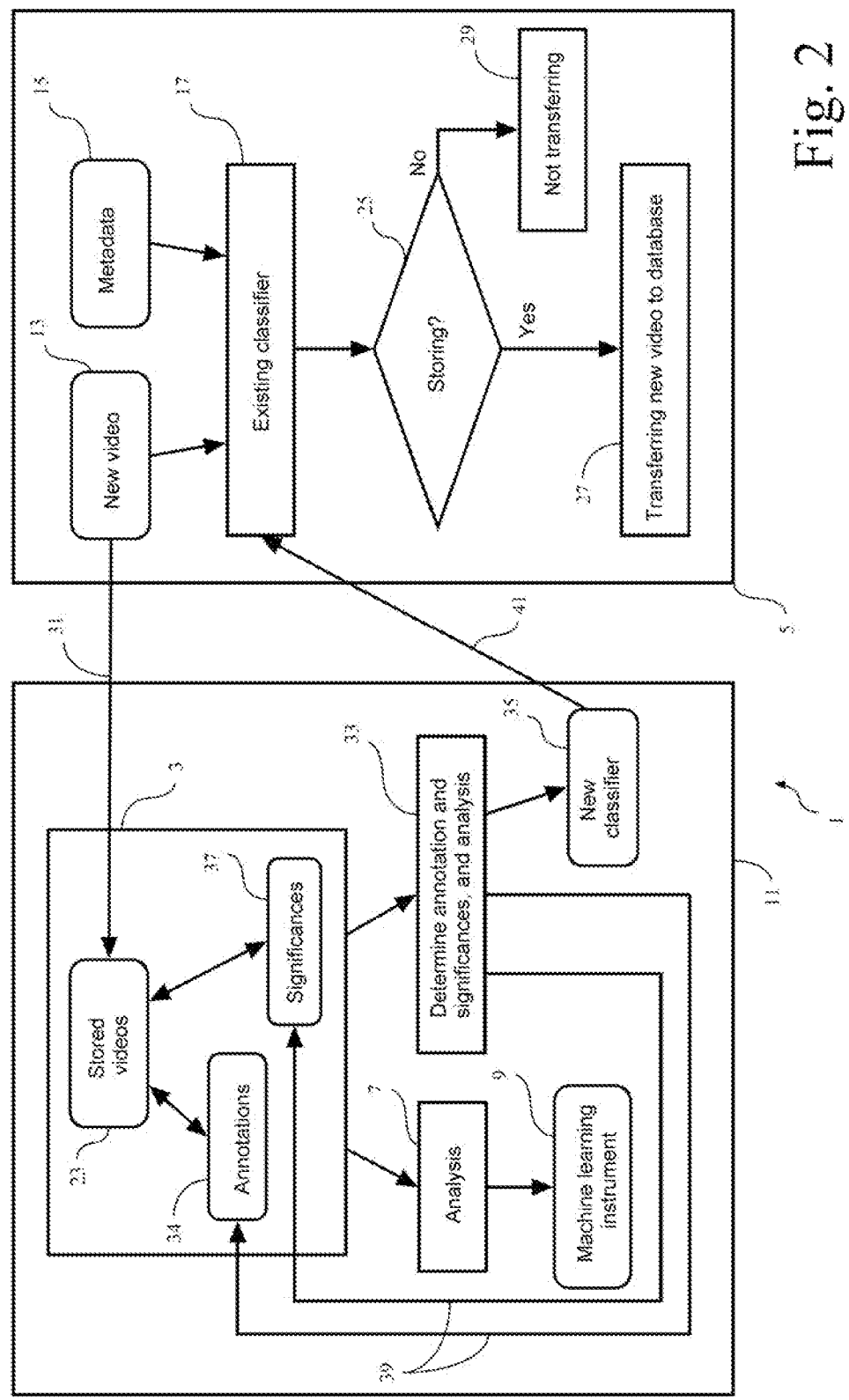
FIG. 2 shows a further detailed diagram for elucidating the method from FIG. 1 and the system 1.

These data sets can be stored in the database 3. The database 3 can be a database system comprising a plurality of hardware and software modules, which can be arranged in a distributed manner. By way of example, each surgical microscopy system 5 can comprise a software module of the database system which runs on the hardware of the surgical microscopy system and enables the interaction of the surgical microscopy system 5 with the database system 3. The data sets can be stored in data memories of the database system which are arranged at locations which differ from the locations at which the surgical microscopes of the surgical microscopy systems 5 are arranged. Since not all of the surgical microscopes of the surgical microscopy systems 5 are arranged at the same location, data sets necessarily have to be transferred from surgical microscopes to data memories via remote data transfer paths. As explained above, the remote data transfer paths have a limited bandwidth, and it is not necessarily practical to store all the data acquired by the surgical microscopy systems in a data memory of the database 3. Referring to FIG. 2, an explanation is given below of a method for storing in the database 3 only those data sets acquired by the surgical microscopy systems 5 which give reason to expect a high significance with regard to the training of the machine learning instrument 9.

FIG. 2 shows elements and modules of a surgical microscopy system 5 which are arranged in a manner spatially separated from a system 11 comprising the database 3 and the analysis module 7 for determining the machine learning instrument 9. In the context of a medical intervention, a new video 13, for example, is recorded by the surgical microscope of the surgical microscopy system 5. Besides the new video 13, further information, such as metadata 15, for instance, is available with respect to the medical intervention carried out. These data 15 can denote for example a type of a medical intervention, an age, a sex and/or a state of health of a patient on whom the medical intervention is performed, a quality of tissue imaged in the images, a characteristic of the user, a location at which the surgical microscopy system is situated, and/or a characteristic of the use history of the surgical microscopy system.

On the basis of the new video 13 and the additional information 15, a classifier 17 assigns the new video 13 to one of two classes that describe whether the new video ought to be stored or ought not to be stored. The result of the classification by the classifier 17 is evaluated in a step 25 and then if, in accordance with the classification, storing the new video 13 in the data memory 23 is demanded, a step 27 for transferring the new video to the data memory 23 is carried out, while in the case where the new video 13 ought not to be stored in the data memory 23, a step 29 is carried out in which the new video 13 is possibly stored for archiving purposes for example locally at the surgical microscope of the surgical microscopy system 5, but is not transferred to the data memory 23 of the database 3 which stores the data with which the machine learning instrument 9 is trained. Step 27 of transferring the new video 13 to the data memory 23 of the database 3 comprises communicating the new video via a remote data transfer path, identified by an arrow 31 in FIG. 2.

For example at regular time intervals or whenever a predetermined number of new videos 13 have been stored in the data memory 23 of the database 3, a module 33 carries out an evaluation of the contents of the database 3. Said evaluation comprises for example an analysis of the videos stored in the data memory 23 in order to determine annotations 34 which can be assigned to the stored videos. Furthermore, already existing annotations with respect to a given stored video can be maintained, changed or deleted. Furthermore, it is possible to generate new annotations 34 with respect to an already stored video. Besides the automatic generation of annotations in the module 33, it is also possible for the annotations 34 with respect to stored videos to originate from other sources, such as human experts, for example.

In the module 33, furthermore, significances 37 are assigned to the individual stored videos 23. The annotations and significances newly determined in the module 33 can then replace the annotations 34 and significances 37 stored in the database 3, as is represented by arrows 39 in FIG. 2.

On the basis of the stored videos 23, annotations 34 and significances 37, a new classifier 35 is furthermore determined in the module 33. The new classifier 35 can then be transferred to the microscopy system 5, as is represented by an arrow 41 in FIG. 2. The new classifier 35 can then replace the existing classifier 17, such that future decisions as to whether or not a new video ought to be stored are taken by the new classifier.

With knowledge of the decision process by means of the classifier 17, the module 33 can determine the significances of the individual videos 23 with the aim that, when significances are once again assigned to the videos 23 after further new videos have been stored in the data memory, the significance newly assigned to a respective video 23 is lower than the significance previously assigned to this video. For this purpose, it is possible to use strategies known in other areas of data processing as "uncertainty sampling", "Least Confidence (LC)", "Margin Sampling" or "Entropy Sampling".

As a result, the method is thus designed such that a significant number of new videos 13 are not transferred via the transfer path 31 to the memory 23 of the database 3. In return, the new classifier 35 is transferred to the surgical microscopy system 5. However, the amount of data communicated during this transfer 41 is significantly smaller than the amount of data corresponding to a plurality of new videos.

The classifier 17 can offer further functionalities. By way of example, the classifier 17 can be configured to make further predictions besides the decision as to whether or not a data set ought to be stored. By way of example, the classifier can establish whether a specific tool or a specific type of tissue is visible in the images of the analysed data set. If the tool thus established is a tool which is not known to the classifier or a tool which is not known with a sufficient significance, then it is possible for example always to decide to store the associated data set. Similarly, it is also possible to decide to store the associated data set whenever the tissue established in this way is tissue which is not known to the classifier or tissue which is not known with a sufficient significance.

The microscopy system 5 can furthermore also be configured, by means of its user interface, to convey to the user a request to annotate the new data sets. The user can decline or accept this request. If the user accepts the request, the user can input his/her annotations with respect to the data sets via the user interface. Preferably, the user is asked for annotations only if the decision in step 25 was positive, that is to say "Yes". The annotations obtained from the user can be transferred together with the new data set 13 to the database 3 and be stored there as the annotation 34 assigned to the then stored data set 23.

The invention claimed is:

1. A method for acquiring data using a surgical microscopy system and a system spatially separated from the surgical microscopy system, comprising:

recording, by the surgical microscopy system, a new data set comprising a multiplicity of images;

analyzing, by the surgical microscopy system, the new data set and deciding, by the surgical microscopy system, using an existing classifier on the basis of the analysis of the new data set whether or not the new data set ought to be stored in a data memory of a database of the system;

transmitting the new data set from the surgical microscopy system to the database and storing the transmitted new data set in the data memory of the database when a result of the deciding indicates that the new data set ought to be stored, and not transmitting the new data set from the surgical microscopy system to the database and not storing the new data set in the data memory when the result of the deciding indicates that the new data set ought not to be stored;

determining, by a module of the system, a new classifier on the basis of training data comprising at least one of data sets stored in the data memory of the database and data obtained from the data sets stored in the data memory of the database; and transmitting the new classifier to the surgical microscopy system and using the new classifier instead of the existing classifier when deciding whether or not a subsequently recorded new data set ought to be stored in the data memory.

2. The method according to claim 1, furthermore comprising assigning, by the surgical microscopy system, at least one annotation to each of the data sets stored in the data memory.

3. The method according to claim 2, wherein the training data comprise the annotations.

4. The method according to claim 2, furthermore comprising assigning, by the surgical microscopy system, a significance to each of the data sets stored in the data memory, and wherein the training data comprise the significances.

5. The method according to claim 4, wherein the determining the new classifier is performed after a plurality of new data sets have been stored in the data memory.

6. The method according to claim 4, wherein the new classifier is determined in such a way that the new data sets stored in the data memory have the effect that when significances are subsequently assigned to the data sets, the significance newly assigned to a respective data set is lower than the significance previously assigned to this data set.

7. The method according to claim 1, wherein deciding whether or not the new data set ought to be stored in the data memory using the existing classifier is furthermore based on further information specifying a type of a medical intervention, an age, a sex and/or a state of health of a patient on whom the medical intervention is performed, a quality of tissue imaged in the images, a characteristic of the user of the surgical microscopy system, a location at which the surgical microscopy system is situated, and/or a use history of the surgical microscopy system.

8. The method according to claim 1, wherein the multiplicity of images comprises a video having a plurality of frames, a volume image having a plurality of slice images, and a multiplicity of OCT scans.

9. The method according to claim 1, furthermore comprising training a machine learning instrument with the data stored in the database.

10. A system for acquiring data for machine learning, wherein the system comprises:
at least one surgical microscopy system;
a database having a data memory; and
a module;
wherein the database and the module are arranged remotely from the at least one surgical microscopy system;
wherein the at least one surgical microscopy system is configured for:
recording a new data set comprising a multiplicity of images;
analyzing the new data set; and
deciding, using an existing classifier on the basis of the analysis of the new data set, whether or not the new data set ought to be stored in the data memory;
transmitting the new data set to the database when a result of the deciding indicates that the new data set ought to be stored;
not transmitting the new data set to the database when the result of the deciding indicates that the new data set ought not to be stored;
receiving a new classifier and replacing the existing classifier with the new classifier received; and
using the new classifier when it is decided whether or not a subsequently recorded new data set ought to be stored in the data memory;
wherein the database is configured for:
receiving the new data set transmitted by the at least one surgical microscopy system; and
storing the new data set received in the data memory, wherein the module is configured for:
determining the new classifier on the basis of training data comprising at least one of data sets stored in the data memory of the database and data obtained from the data sets stored in the data memory of the database; and
transmitting the new classifier to the at least one surgical microscopy system.

11. The system according to claim 10, wherein the module is furthermore configured for:
assigning at least one annotation to each of the data sets stored in the data memory.

12. The system according to claim 11, wherein the training data comprise the annotations.

13. The system according to claim 11,
wherein the module is furthermore configured for:
assigning a significance to each of the data sets stored in the data memory, and wherein the training data comprise the significances.

14. The system according to claim 13, wherein the module is configured to carry out the process of determining the new classifier after a plurality of new data sets have been stored in the data memory.

15. The system according to claim 13, wherein the module is configured to determine the new classifier in such a way that the new data sets stored in the data memory have the effect that when significances are subsequently assigned to the data sets by means of the module, the significance newly assigned to a respective data set is lower than the significance previously assigned to this data set.

16. The system according to claim 10, wherein the at least one surgical microscopy system is configured to carry out the process of deciding whether or not the new data set ought to be stored in the data memory using the existing classifier furthermore on the basis of further information specifying a type of a medical intervention, an age, a sex and/or a state of health of a patient on whom the medical intervention is performed, a quality of tissue imaged in the images, a characteristic of the user of the surgical microscopy system, a location at which the surgical microscopy system is situated, and/or a use history of the surgical microscopy system.

17. The system according to claim 10, wherein the multiplicity of images comprises a video having a plurality of frames, a volume image having a plurality of slice images, and a multiplicity of OCT scans.

18. The system according to claim 10, furthermore comprising an analysis module configured for training a machine learning instrument with the data stored in the database.

* * * * *